United States Patent
Rapoport et al.

(10) Patent No.: US 11,406,814 B2
(45) Date of Patent: Aug. 9, 2022

(54) VISUAL PROSTHESIS EMPLOYING VENTRICULAR OR ENDOVASCULAR NEURAL ELECTRODE ARRAYS

(71) Applicant: Precision Neuroscience Corporation, New York, NY (US)

(72) Inventors: Benjamin I. Rapoport, New York, NY (US); Demetrios Papageorgiou, Weston, MA (US); Jason Chen, Melrose, MA (US)

(73) Assignee: Precision Neuroscience Corporation, New York, NY (US)

( * ) Notice: Subject to any disclaimer, the term of this patent is extended or adjusted under 35 U.S.C. 154(b) by 587 days.

(21) Appl. No.: 16/408,721

(22) Filed: May 10, 2019

(65) Prior Publication Data
US 2019/0329026 A1    Oct. 31, 2019

Related U.S. Application Data

(63) Continuation of application No. 15/585,746, filed on May 3, 2017, now Pat. No. 10,328,255.
(Continued)

(51) Int. Cl.
*A61N 1/05*    (2006.01)
*A61N 1/36*    (2006.01)
(Continued)

(52) U.S. Cl.
CPC ............. *A61N 1/0534* (2013.01); *A61B 5/24* (2021.01); *A61B 5/291* (2021.01); *A61B 5/686* (2013.01);
(Continued)

(58) Field of Classification Search
CPC ........ A61B 2562/046; A61B 2562/164; A61B 5/24; A61B 5/282; A61B 5/291;
(Continued)

(56) References Cited

U.S. PATENT DOCUMENTS

| 6,463,328 | B1 | 10/2002 | John |
| 6,950,707 | B2 | 9/2005 | Whitehurst |

(Continued)

FOREIGN PATENT DOCUMENTS

| WO | 2009/135075 A1 | 11/2009 |
| WO | 2015/156862 A2 | 10/2015 |
| WO | 2016/044296 | 3/2016 |

OTHER PUBLICATIONS

U.S. Appl. No. 15/585,786, filed May 3, 2017, Rapoport et al.
(Continued)

*Primary Examiner* — Amanda K Hulbert
(74) *Attorney, Agent, or Firm* — Wolf, Greenfield & Sacks, P.C.

(57) ABSTRACT

The present disclosure relates to a method of generating visual percepts using conformal electrode arrays. The electrode arrays can be placed into the ventricular system or cerebral venous sinuses, which function as minimally invasive techniques for precise spatial and temporal localization of electrical activity within the brain, and precise electrical stimulation of brain tissue, to diagnose and restore function in conditions caused by abnormal electrical activity in the brain. The disclosure further comprises a system for using these arrays to generate time-varying electric fields to stimulate the visual pathways of the brain, including the optic radiations and the occipital cortex, in ways that lead to visual perception.

11 Claims, 14 Drawing Sheets

Related U.S. Application Data

(60) Provisional application No. 62/406,623, filed on Oct. 11, 2016, provisional application No. 62/395,672, filed on Sep. 16, 2016.

(51) Int. Cl.
| | |
|---|---|
| *A61N 1/372* | (2006.01) |
| *A61B 5/00* | (2006.01) |
| *A61B 5/24* | (2021.01) |
| *A61B 5/291* | (2021.01) |
| *A61B 5/282* | (2021.01) |

(52) U.S. Cl.
CPC .......... *A61N 1/0531* (2013.01); *A61N 1/3606* (2013.01); *A61N 1/36046* (2013.01); *A61N 1/36064* (2013.01); *A61N 1/36067* (2013.01); *A61N 1/36071* (2013.01); *A61N 1/37205* (2013.01); *A61B 5/282* (2021.01); *A61B 2562/046* (2013.01); *A61B 2562/164* (2013.01)

(58) Field of Classification Search
CPC .... A61B 5/686; A61N 1/0531; A61N 1/0534; A61N 1/36046; A61N 1/3606; A61N 1/36064; A61N 1/36067; A61N 1/36071; A61N 1/37205
See application file for complete search history.

(56) References Cited

U.S. PATENT DOCUMENTS

| | | | |
|---|---|---|---|
| 8,583,241 | B2 | 11/2013 | Greenberg et al. |
| 8,934,965 | B2 | 1/2015 | Rogers et al. |
| 9,867,978 | B1 | 1/2018 | Rapoport et al. |
| 9,919,146 | B2 | 3/2018 | Hua |
| 10,118,030 | B2 | 11/2018 | Pellinen et al. |
| 10,328,255 | B2 | 6/2019 | Rapoport et al. |
| 2003/0088301 | A1 | 5/2003 | King |
| 2005/0004624 | A1 | 1/2005 | Gliner et al. |
| 2005/0137646 | A1 | 6/2005 | Wallace et al. |
| 2005/0137647 | A1 | 6/2005 | Wallace et al. |
| 2006/0106432 | A1 | 5/2006 | Sawan et al. |
| 2007/0135861 | A1 | 6/2007 | Wallace et al. |
| 2007/0150039 | A1 | 6/2007 | Leigh |
| 2008/0097424 | A1 | 4/2008 | Wizeman et al. |
| 2009/0186321 | A1 | 7/2009 | Rojas et al. |
| 2010/0057046 | A1 | 3/2010 | Steven et al. |
| 2011/0056845 | A1 | 3/2011 | Stellacci et al. |
| 2011/0166565 | A1 | 7/2011 | Wizeman et al. |
| 2012/0277621 | A1 | 11/2012 | Gerber et al. |
| 2012/0323288 | A1 | 12/2012 | Anderson et al. |
| 2012/0330393 | A1 | 12/2012 | Janik et al. |
| 2013/0030353 | A1 | 1/2013 | Seymour et al. |
| 2013/0267928 | A1 | 10/2013 | Imran |
| 2014/0288667 | A1 | 9/2014 | Oxley |
| 2015/0011927 | A1 | 1/2015 | Hua |
| 2015/0112360 | A1 | 4/2015 | Pellinen et al. |
| 2016/0331968 | A1 | 11/2016 | Greenberg et al. |
| 2017/0056845 | A1 | 3/2017 | Huang |
| 2018/0078767 | A1 | 3/2018 | Rapoport et al. |
| 2018/0117309 | A1 | 5/2018 | Rapoport et al. |

OTHER PUBLICATIONS

U.S. Appl. No. 15/856,677, filed Dec. 28, 2017, Rapoport et al.
PCT/US2017/050109, dated Nov. 20, 2017, International Search Report and Written Opinion.
PCT/US2017/050109, dated Mar. 28, 2019, International Preliminary Report on Patentability.
PCT/US2017/050110, dated Sep. 27, 2017, International Search Report and Written Opinion.
PCT/US2017/050110, dated Mar. 28, 2019, International Preliminary Report on Patentability.
International Search Report and Written Opinion dated Nov. 20, 2017 in connection with International Application No. PCT/US2017/050109.
International Preliminary Report on Patentability dated Mar. 28, 2019 in connection with International Application No. PCT/US2017/050109.
International Search Report and Written Opinion dated Sep. 27, 2017 in connection with International Application No. PCT/US2017/050110.
International Preliminary Report on Patentability dated Mar. 28, 2019 in connection with International Application No. PCT/US2017/050110.
Auriat et al., A Review of Transcranial Magnetic Stimulation and Multimodal Neuroimaging to Characterize Post-Strake Neuroplasticity. Frontiers in Neurology. Oct. 29, 2015;6:226. 20 pages.
Boddu et al., Resolution of Pulsatile Tinnitus after Venous Sinus Stenting in Patients with Idiopathic Intracranial Hypertension. PLoS One, Oct. 21, 2016; 11(1O):e0164466.
Boniface et al., Endovascular electroencephalography: the technique and its application during carotid amytal assessment. J Neurol Neurosurg Psychiatry. 1997; 62(2):193-5.
Bower et al., Intravenous recording of intracranial, broadband EEG. Journal of Neuroscience Methods. 2013;214:21-26.
Braun, Aesculap Neurosurgery, Berlin (undated).
Chabardès et al., Endoventricular Deep Brain Stimulation of the Third Ventricle: Proof of Concept and Application to Cluster Headache. Neurosurgery. Dec. 2016;79(6):806-815.
Choi et al., A Review of Stimulating Strategies for Cochlear Implants. (2012) Cochlear Implant Research Updates., Chapter 5, p. 77-90.
De Ponti, et al., Computerized high-density mapping of the pulmonary veins: new insights into their electrical activation in patients with atrial fibrillation. Europace. 2004;6(2):97-108.
Furlan, Endovascular Therapy for Stroke—It's about Time. N Engl J Med. Jun. 2015; 372:2347-2349.
García-Asensio et al., The role of intravascular EEG. Revista de Neurologia. Mar. 1999; 12(2):139-142.
García-Asensio et al., Technical aspects of intra-arterial electroencephalogram recording. Intervention Neuroradiology. 1999; 5: 289-300.
García-Asensio et al., The contribution of an intraarterial electroencephalographic study in patients with deep epileptogenic foci. Rev Neurol. Apr. 1-5, 2000;30(7):625-34. (English abstract only).
Hasdemir et al., Endovascular Stimulation of Autonomic Neural Elements in the Superior Vena Cava Using a Flexible Loop Catheter. Jpn Heart J. May 2003;44(3): 417-427.
Horton et al., Feasibility and efficacy of transcranial motor-evoked potential monitoring in neuroendovascular surgery. AJNR Am J Neuroradiol. Oct. 2012;33(9): 1825-31.
Ishida et al., Intracranial EEG recording from intravascular electrodes in patients with temporal lobe epilepsy. Proceedings of the 31st Congress of the Japan Epilepsy Society, Kyoto, Japan (Sep. 18-19, 1997). Epilepsia. 39 (S5) 77 (1998).
Kunieda et al., Use of Cavernous Sinus EEG in the Detection of Seizure Onset and Spread in Mesial Temporal Lobe Epilepsy. Epilepsia, 2000; 41(11):1411-1419.
Llinás et al., Neuro-vascular central nervous recording/stimulating system: Using nanotechnology probes. Journal of Nanoparticle Research. 2005; 7:111-127.
Mikuni et al., Cavernous Sinus EEG: A New Method for the Preoperative Evaluation of Temporal Lobe Epilepsy. Epilepsia. 1997; 38(4):472-482.
Murphy et al., Human cardiac nerve stimulation. Ann Thorac Surg. Sep. 1992;54(3):502-6.
Murphy et al., Preliminary observations on the effects of stimulation of cardiac nerves in man. Can. J. Physiol. Pharmacol. 1985; 63:649-655.
Nabutovsky et al., Lead Design and Initial Applications of a New Lead for Long-Term Endovascular Vagal Stimulation. PACE. 2007; 30:S215-S218.
Nakase et al., An Intra-Arterial Electrode for Intracranial Electro-Encephalogram Recordings., Acta Neurochir. 1995;136:103-105.

(56) References Cited

OTHER PUBLICATIONS

Oxley et al., Minimally invasive endovascular stent-electrode array for high- fidelity, chronic recordings of cortical neural activity. Nat Biotechnol. Mar. 2016;34(3):320-7.

Penn et al., Intravascular intracranial EEG recording Technical note, J. Neurosurg. 1973;38: 239-243.

Pezaris et al., Getting signals into the brain: visual prosthetics through thalamic microstimulation. Neurosurg Focus. Jul. 2009;27(1):E6.

Ponikowski et al., Transvenous phrenic nerve stimulation for the treatment of central sleep apnoea in heart failure. Eur Heart J. Aug. 19, 2011;1-6.

Rapoport et al., Efficient universal computing architectures for decoding neural activity. PLoS One. Sep. 12, 2012;7(9):e42492.

Rapoport et al., A glucose fuel cell for implantable brain-machine interfaces. PLoS One. Jun. 12, 2012;7(6):e38436.

Rubinstein, How cochlear implants encode speech. Curr Opin Otolaryngol Head Neck Surg. Oct. 2004;12(5):444-8.

Ruddy, Conducting Polymer Wires for Intravascular Neural Recording. Massachusetts Institute of Technology 2006. http://hdl.handle.net/1721.1 /35308.

Santillan et al., Long-term clinical and angiographic results of Neuroform stent-assisted coil embolization in wide-necked intracranial aneurysms. Neurosurgery. May 2012;70(5):1232-7; discussion 1237.

Schauerte et al., Catheter stimulation of cardiac parasympathetic nerves in humans: a novel approach to the cardiac autonomic nervous system. Circulation. Nov. 13, 2001;104(20):2430-5.

Schauerte et al., Transvenous parasympathetic cardiac nerve stimulation: an approach for stable sinus rate control. J Cardiovasc Electrophysiol. Nov. 1999; 10(11):1517-24.

Schauerte et al., Transvenous parasympathetic nerve stimulation in the inferior vena cava and atrioventricular conduction. J Cardiovasc Electrophysiol. Jan. 2000;11(1):64-9.

Schauerte et al., Ventricular rate control during atrial fibrillation by cardiac parasympathetic nerve stimulation: a transvenous approach. J Am Coll Cardiol. Dec. 1999;34(7):2043-50.

Scherlag et al., Endovascular neural stimulation via a novel basket electrode catheter: Comparison of electrode. J Interv Card Electrophysiol. Apr. 2000;4(1):219-24.

Scherlag et al., Endovascular stimulation within the left pulmonary artery to induce slowing of heart rate and paroxysmal atrial fibrillation. Cardiovascular Research. 2002;54(2): 470-475.

Sefcik et al., The evolution of endovascular electroencephalography: historical perspective and future applications. Neurosurq Focus. May 2016; 40(5):E7.

Shih et al., Brain-Computer Interfaces in Medicine. Mayo Clin. Proc. Mar. 2012;87:268-279.

Song et al., Intraventricular Monitoring for Temporal Lobe Epilepsy: Report on Techniques and Initial Results in Eight Patients. J. Neurol Neurosurg Psychiatry. 2003;74:561-565.

Stoeter et al., Intracranial electroencephalographic and evoked-potential recording from intravascular guide wires. AJNR Am J Neuroradiol. Jun-Jul. 1995; 16(6):1214-7.

Teplitzky et al., Computational modeling of an endovascular approach to deep brain stimulation. J. Neural Eng. 2014;11:1-13.

Thömke et al., Endovascular electroencephalography during an intracarotid amobarbital test with simultaneous recordings from 16 electrodes. J Neurol Neurosurg Psychiatry. Apr. 1998;64(4):565.

Thompson et al., Bradycardia induced by intravascular versus direct stimulation of the vagus nerve. Ann Thorac Surg. Mar. 1998;65(3):637-42.

Timmermann et al., Multiple-source current steering in subthalamic nucleus deep brain stimulation for Parkinson's disease (the VANTAGE study): a non- randomised, prospective, multicentre, open-label study. Lancet Neurol. Jul. 2015;14(7):693-701.

Watanabe et al., Intravascular Neural Interface with Nanowire Electrode. Electronics and Communications in Japan. 2009; 92(7): 29-37.

Yamada, Pulmonary Vein Isolation with a Multielectrode Basket Catheter. Indian Pacing Electrophysiol J. Apr.-Jun. 2007; 7(2): 97-109.

Zeitlhofer et al., Transarterial EEG in superselective cerebral angiography. EEG-EMG-Zeitschrift fur Elektroenzephalographie Elekgro myo graphic and Verwandte Gebeite, 21(1): 70-72 (Mar. 1990) (English abstract only).

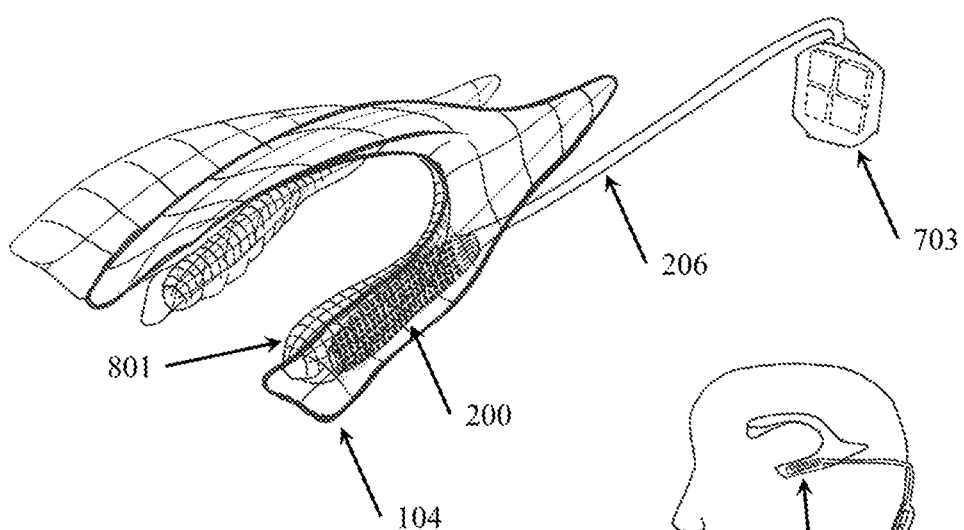
FIG. 8A
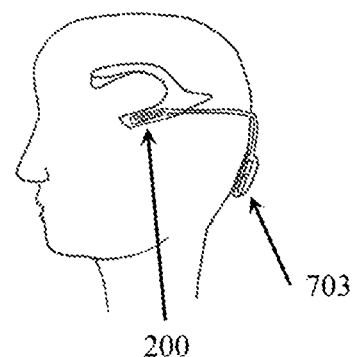
FIG. 8B
FIGS. 8A-8B

VISUAL PROSTHESIS EMPLOYING VENTRICULAR OR ENDOVASCULAR NEURAL ELECTRODE ARRAYS

PRIORITY

The present application is a continuation claiming the benefit under 35 U.S.C. § 120 of U.S. application Ser. No. 15/585,746, filed May 3, 2017, which claims priority under 35 U.S.C. § 119(e) of U.S. Provisional Patent Application No. 62/406,623, filed Oct. 11, 2016 and U.S. Provisional Patent Application No. 62/395,672, filed Sep. 16, 2016. The entire contents of these applications are incorporated herein by reference in their entirety.

RELATED APPLICATIONS

This application is related to U.S. Application Ser. No. 15/585,917 filed on May 3, 2017, entitled "Conformal Electrode Arrays for Electrophysiologic Recording and Neural Stimulation withing the Cerebral Ventricles".

FIELD

The present application relates to a visual prosthesis and specifically to a method and device of recording and/or stimulation of neural activities of visual pathways using electrode arrays.

BACKGROUND

Several common disorders of the brain, spinal cord, and peripheral nervous system arise due to abnormal electrical activity in biological (neural) circuits. In general terms, these conditions may be classified into:
(1) Conditions such as epilepsy, in which electrical activity is dysregulated, and recurrent activity persists in an uncontrolled fashion;
(2) Conditions such as stroke or traumatic injury, in which an electrical pathway is disrupted, disconnecting a component of a functional neural circuit; and
(3) Conditions such as Parkinson's disease, in which neurons in a discrete region cease to function, leading to functional impairment in the neural circuits to which they belong.

When the electrical lesion is focal and relatively discrete, as is very often the case, effective diagnosis and treatment of such conditions depends on precise localization of the lesion and, when possible, restoration of normal electrophysiologic function to the affected region.

A variety of well-established techniques exist for localizing electrical lesions in the brain, each of which has specific limitations:
(1) Imaging techniques such as magnetic resonance imaging (MRI) and computed tomography (CT) constitute entirely noninvasive methods of examining brain tissue, and many functional lesions (including strokes, anatomic abnormalities capable of causing seizures, and foci of neuronal degeneration) can be detected and precisely localized using such imaging modalities. Not all functional lesions can be detected these using imaging modalities, however, as these techniques do not image electrical activity. Furthermore, these imaging techniques lack temporal resolution, and provide no mechanism for therapeutic electrophysiologic intervention.
(2) Electromagnetic recording techniques such as electroencephalography (EEG) and magnetoencephalography (MEG) are entirely noninvasive techniques that provide excellent temporal resolution of electrical activity in the brain. For this reason, EEG is currently the gold standard modality for detection of seizure activity. The spatial resolution of such techniques is limited, however, both due to physical distance of electrodes from the brain, and by the dielectric properties of scalp and skull. The spatial resolution of EEG is better for superficial regions, and worse for neural activity deep within the brain.
(3) Electrocorticography (ECoG), or intracranial EEG, is a form of electroencephalography that provides improved spatial resolution by placing recording electrodes directly on the cortical surface of the brain (in conventional EEG, by contrast, electrodes are positioned on the scalp). This modality is frequently used during neurosurgical procedures, to map normal brain function and locate abnormal electrical activity, but it requires craniotomy, temporary surgical removal of a significant portion of the skull, in order to expose the brain surfaces of interest, and exposes patients to the attendant risks of brain surgery. Furthermore, while electrical activity near the cortical surface of the brain can be mapped with reasonable spatial resolution, electrical activity deep within the brain remains difficult to localize using ECoG.
(4) "Depth electrodes" record electrical activity with high spatial and temporal precision, but such electrodes record only from small volumes of tissue (small populations of neurons), and their placement requires disruption of normal brain tissue along the trajectory of the electrode, resulting in irreversible damage or destruction of some neurons. As such electrodes are placed surgically, in a hypothesis-driven manner, the number of such electrodes that can be safely placed simultaneously is limited.
(5) Deep brain stimulation (DBS) electrodes, the stimulating analog of recording depth electrodes, electrically stimulate brain regions with millimetric precision. They are implanted using minimally invasive surgical techniques, and can be effective in conditions such as Parkinson's disease, in which neuronal dysfunction is confined to a small, discrete, and unambiguous region of the brain.

While the foregoing list is not exhaustive, it provides a general overview of the range of techniques presently available for electrical recording and stimulation of the living human brain.

In practice, all neural recording and stimulation techniques involve design trade-offs among a number of primary factors:
(1) Spatial resolution;
(2) Temporal resolution;
(3) Degree of invasiveness; and
(4) Optimization for electrical recording or electrical stimulation.

Blindness and visual impairment are often caused by disorders in the eyes, leaving the brain optic radiations and visual cortex intact but disconnected from normal input. Consequently, in forms of blindness due to macular degeneration, glaucoma, and diabetic retinopathy, and several other conditions, though the retina or optic nerve may be diseased, electrical stimulation of the optic radiations and visual cortex can still generate predictable visual sensations.

SUMMARY

The present disclosure relates to precise, patterned stimulation of regions of the brain related to vision, in response to images obtained from video or other recording devices, either in order to restore sight to a blind individual or to augment visual perception of an individual with normal vision.

In some embodiments, a conformal electrode array can be deployed in the occipital horn of the lateral ventricle, with electrical field lines extending into the visual cortex or optic radiations, and corresponding visual percept in the visual field.

In some embodiments, a conformal electrode array can be deployed in the temporal horn of the lateral ventricle, with electrical field lines extending into the temporal optic radiation, and a corresponding visual percepts in the visual field.

In some embodiments, a conformal electrode array can be deployed within a cerebral venous sinus such as the transverse, superior sagittal, or straight sinus, with electric field lines from the arrays extending into the visual cortex, and a corresponding visual percept in the visual field.

In some embodiments, conformal arrays in the ventricular system can function together with conformal arrays within the venous sinuses to stimulate points within the brain visual pathways with precise spatial selectivity.

In one aspect, the present application discloses an implantable medical device for electrically stimulating portions of a brain that relate to vision, the medical device comprises a conformal flexible substrate configured to be inserted into a fluid-filled intracranial cavity proximate to a component of a visual pathway of the brain, and a plurality of electrodes, arranged in a three-dimensional array, fabricated on the substrate.

In some embodiments, the plurality of electrodes has an inter-electrode spacing corresponding to a diameter of a neuron, the diameter can be about 50 micrometers. In some embodiments, the plurality of electrodes includes more than 100,000 electrodes per square centimeter. In some embodiments, the plurality of electrodes can include more than 200,000 electrodes per square centimeter. In some embodiments, the flexible substrate can be made of polyimide. In some embodiments, the medical device can be implanted into a venous sinus proximate to a visual cortex. In some embodiments, the medical device further includes a conformal electrode array implanted into a ventricular compartment of the brain proximate to optic radiations, a lateral geniculate body, or a visual cortex. In some embodiments, the implantable medical device can include an external camera in electrical communication with the plurality of electrodes, wherein the camera can beconfigured to send visual images, and the external camera can be mounted on the eye of a user, a glass, or a goggle. In some embodiments, the implantable medical device can provide an image having a high pixel count of at least 10,000 pixels to replicate, approximate, restore, or augment normal human vision.

In another aspect, the present application discloses a method of electrically stimulating portions of a brain that relate to vision using an endovascular electrode array within a venous sinus proximate to a visual cortex, the method can include determining a portion of the visual cortex for electrical stimulation, accessing previously stored registration information regarding a location of the endovascular electrode array within the venous sinus, selecting one or more electrodes in the endovascular electrode array based on the registration information, and stimulating the determined portion of visual cortex with the selected electrodes.

In some embodiments, the method can include forming an electrical field beam distributed in a three-dimensional space using the selected electrodes. In some embodiments, the method can include localizing electrical activity in the brain using the selected electrode distributed in a three-dimensional space. In some embodiments, the method can include determining a portion of optic radiations, a lateral geniculate body, or a visual cortex for electrical stimulation using a conformal electrode array implanted into a ventricular compartment of the brain proximate to the optic radiations, lateral geniculate body, or visual cortex; accessing previously stored registration information regarding a location of the electrode array within the ventricular compartment of the brain; selecting one or more electrodes in the electrode array based on the registration information; and stimulating the visual pathway with the selected electrodes. In some embodiments, the method can include implanting the conformal electrode array configured to stimulate targets within the visual pathways of the brain, the targets can be optic tracts, lateral geniculate bodies, or visual cortex. In some embodiments, the method can include registering the endovascular electrode to obtain its orientation and position within the venous sinus via neuroimaging. In some embodiments, the method can include inserting the endovascular electrode into the venous sinus via a minimally invasive insertion techniques, such as cannula or catheter. In some embodiments, the method can include receiving visual images from an external camera in electrical communication with the plurality of electrodes, the external camera can be mounted on the eye of a user, a glass, or a goggle. In some embodiments, the method can include providing an image having a high pixel count of at least 10,000 pixels to approximate, restore, or augment normal human vision.

BRIEF DESCRIPTION OF DRAWINGS

FIGS. 8A-8B depict a conformal electrode array implanted in the temporal horn of the left lateral ventricle, in accordance with embodiments of the present disclosure;

DESCRIPTION

Figure 1:
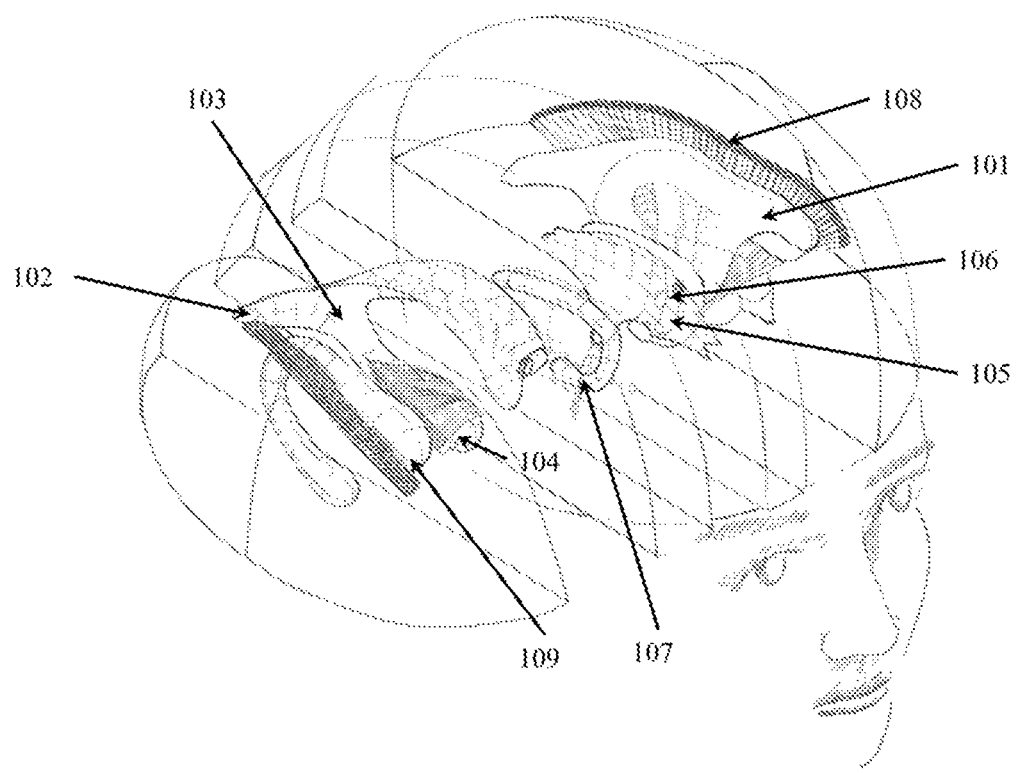
FIG. 1 depicts a cross-section drawing illustrating several anatomic structures within the human brain, and their positions with respect to the cerebral ventricles.

The present disclosure describes a device and method for the restoration and augmentation of vision. Vision can be partially restored or augmented through electrical stimulation at multiple sites within the visual pathways, which extend from the retina, where light entering the eye is first transduced to electrophysiologic signals, to the visual cortex in the occipital lobe. Major structures in this pathway, each of which has received attention as a locus for electrical stimulation to generate visual percepts, include the retina, optic nerve, optic chiasm, optic tracts, lateral geniculate nuclei, the optic radiations, and the visual cortex in the occipital lobe. These structures are difficult to access using conventional surgical techniques. Of these structures, only the visual cortex can be immediately accessed from the outer surface of the brain. However, conventional electrical stimulation techniques achieve high-resolution stimulation of the visual cortex using interfaces that extensively penetrate the brain surface, resulting inevitably in damage to brain tissue in the region of interest.

The optic radiations are axons used to deliver visual information from the retina of the eye to the visual cortex. The optic radiations are white matter tracts that carry visual information from the optic tracts to the visual cortex. Major divisions of the optic radiations in each hemisphere carry visual information from specific sectors of the visual field. For example, the optic radiation passing through the temporal lobe of the left hemisphere carries visual information from the right-sided visual field to the visual cortex of the left hemisphere. The principal optic radiations pass through the temporal and parietal lobes en route to the visual cortex of the occipital lobe. The optic radiations border the ventricular system, particularly the surfaces of the temporal horn, atrium, and posterior horn of the lateral ventricles. The optic radiations and visual cortex surround the occipital horn of the lateral ventricle. Electrode arrays conforming to the ventricular surfaces in these regions are therefore capable of stimulating the visual pathways so as to generate visual percepts.

In particular, the present disclosure describes a flexible and collapsible array of electrodes, and a minimally invasive method of delivering such an array into the cerebral ventricles, the fluid-filled cavities at the center of the brain. The walls of the cerebral ventricles are formed by the inner surfaces of several deep brain structures that are difficult to access from the cortical surface, including the hippocampus and medial temporal lobe (frequently involved in seizure disorders), the hypothalamus (which is involved in hormonal regulation, circadian rhythm, and the modulation of cravings related to a range of factors, including sleep, food, salt and water, warmth, and sex), the thalamus and basal ganglia (involved in movement disorders such as Parkinson's disease), and the internal capsule (frequently damaged in hemorrhagic stroke). By arraying electrodes along the inner walls of the cerebral ventricles, deep brain targets can be accessed electrically for precise electrical recording and stimulation.

In summary, electrode arrays positioned within the ventricles can interface with structures deep within the brain, without traumatizing brain tissue, in ways that conventional depth electrodes and surface electrodes cannot. The ability of these electrodes to more extensively interface with deep brain structures is due to two principal properties. First, during initial placement, ventricular arrays can be navigated within a purely fluidic compartment, that provides extensive access to deep brain structures. By navigating within this fluidic compartment (the cerebral ventricular system), ventricular electrode arrays avoid traumatizing delicate brain tissue. Second, multiple neural structures that are difficult to access electrically using conventional techniques are situated in close proximity to the surface of the ventricular system. The ventricular system of the brain can be accessed and navigated using techniques of minimally invasive neurosurgery, including neuro-endoscopy.

FIG. 1 is a cross-section drawing illustrating several anatomic structures within a human brain, and their positions with respect to the cerebral ventricles. FIG. 1 includes left lateral ventricle 101, occipital horn 102, atrium 103, temporal horn 104, the third ventricle 105, the left foramen of Monro 106, the right fornix 107, the left internal capsule 108, and the right caudate nucleus 109. There is approximate macroscopic symmetry with respect to the vertical midline (sagittal) plane, so that left lateral ventricle 101 has a mirror image right lateral ventricle (not shown FIG. 1), the right fornix 107 has a mirror image left fornix (not shown in FIG. 1), the left internal capsule 108 has a mirror image right internal capsule, and the right caudate nucleus 109 has a mirror image left caudate nucleus (not shown in FIG. 1). Labeled regions of the right lateral ventricle are occipital horn 102, atrium 103, temporal horn 104. The third ventricle 105 is contiguous with the left and right lateral ventricles through the left foramen of Monro 106, and its mirror image right foramen of Monro (not shown in FIG. 1).

Conformal electrode arrays can be clinically useful in mapping and targeted ablation of cardiac lesions causing heart arrhythmias. For example, conformal electrode arrays can be used for electrophysiologic mapping in real-time in the heart. Exemplary techniques for treating conditions such as atrial fibrillation can use conformal electrode arrays, delivered through the major blood vessels, to record from the electrical system of the heart (De Ponti et al. (2004) *Europace* 6:97-108); (Yamada (2007) *Indian Pacing Electrophysiol. J.* 7:97-109). However, there is extremely limited precedent for intraventricular electrode recording in the brain (Konrad et al. (2003) *J. Neurol. Neurosurg. Psychiatry* 74:561-565). Intraventricular electrode recording in the brain has only been described using linear sets of electrodes, not with conformal electrode arrays. Additionally, there is limited precedent for stimulation of brain regions surrounding the ventricles from within the ventricles, (Benabid et al.

(2016) *Neurosurgery* 79:806-815) but only with conventional deep brain stimulation electrodes, not with conformal electrode arrays.

Figures 2A, 2B, 2C, 2D:
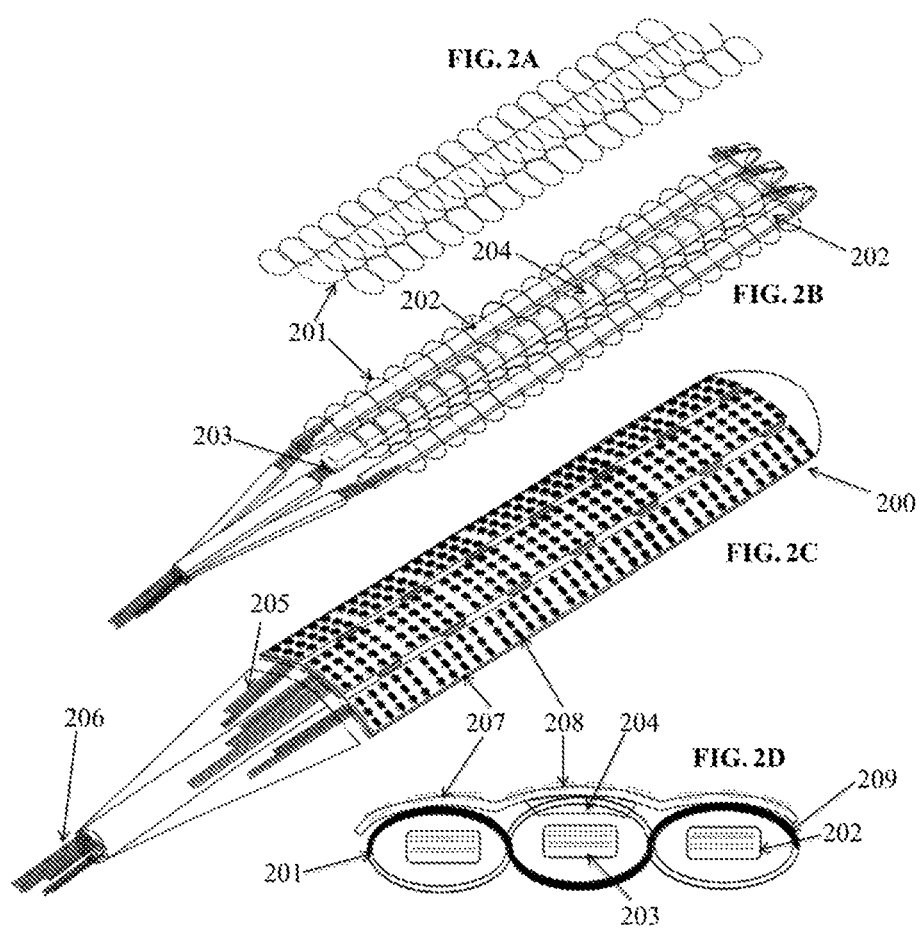
FIGS. 2A-2D depict the unfolded views of a conformal intraventricular electrode array, in accordance with embodiments of the present disclosure.

FIGS. 2A-2D depict a series of unfolded views of layers of a conformal intraventricular electrode array 200, in accordance with embodiments of the present disclosure. FIG. 2A depicts a skeleton member 201 of a conformal electrode array in its unfolded configuration according to one embodiment of the present disclosure. Skeleton member 201 can provide the capability of folding/unfolding of the conformal electrode array 200. Skeleton member 201 can be configured to form an array of loops, for example, one loop, two loops, three loops, four loops, five loops, six loops, seven loops, eight loops, nine or more loops wide. In the embodiment depicted in FIG. 2A, skeleton member 201 can be configured to form three loops. In some embodiments, skeleton member 201 can be made of a resilient inert metal material such as, for example, a shape memory alloy nitinol metal or stainless steel. In some embodiments, skeleton member 201 can composed of a shape-memory material, such as nitinol. For example, in some embodiments, skeleton member 201 can be Grade 1 Nitinol. In some embodiments, skeleton member 201 can be about 100 micrometers to about 200 micrometers, for example, 150 micrometers in diameter. In some embodiments, skeleton member 201 can be formed by winding and training a single strand on a mandrel.

In some embodiments, array 200 can include a mechanism for expanding skeleton member 201 from the axial configuration used for initial implantation, to an expanded, deployed configuration that conforms (based on measurements obtained, for example, from patient-specific medical imaging) to the inner shape of the intracranial ventricular compartment. Certain general geometric characteristics are appropriate for implantation within the cerebral ventricles, but shape-memory materials permit skeleton member 201 to be sized and shaped in a patient-specific manner. Ovoid and cylindrical shapes provide useful approximations to the shapes of certain parts of the cerebral ventricular system.

FIG. 2B depicts another view of conformal array 200. FIG. 2B includes skeleton member 201, side panels 202, a center panel 203, a stiffener 204, and lead wires 206. The loops formed by skeleton member 201 allow placement of panels 202, 203 and stiffener 204 on top of center panel 203 through the loops of skeleton member 201.

In some embodiments, panels 202, 203 can be composed of polyimide or other polymer substrates suitable for fabricating flexible printed circuits. The panels are typically rectangular, but deformable. Typically they measure between about 5 mm and about 50 mm in width, about 20 mm and about 60 mm in length, and about 10 micrometers to 100 micrometers in thickness.

A non-exclusive list of materials that can be used to make stiffener 204 includes polyimide, polyether ether ketone (PEEK), polycarbonates, polyamides, polyethylene, polypropylene, polyesters, and polyethersulfones. The stiffness of stiffener 204 can be controlled such that it is rigid enough to hold the array in place while it is being unsheathed from a cannula, while stiffener 204 can be flexible enough to conform in a gentle arc per the anatomy inside the cerebral ventricles.

In some embodiments of the present disclosure, stiffener 204 and center panel 203 can be bonded together with a biocompatible adhesive. Exemplary biocompatible adhesives can include, but not limited to, medical grade epoxies, including flexible and high-bond-strength cyanoacrylate epoxies. In some embodiments, stiffener 204 and center panel 203 can be bonded by heat curing under pressure. In some embodiments, stiffener can be molded or etched with trenches, which can be used to hold skeleton member 201 in place. In one embodiment of the present disclosure, the side panels do not have stiffeners, and can wrap upwards to conform to the anatomy. In some embodiments, each side panel 202 also can have a stiffener.

FIG. 2C depicts conformal electrode array 200 according to some embodiments of the present disclosure. Conformal electrode array 200 can include flexible circuit 207, electrodes 208, conductor traces 205 and bundled lead wires 206 connected to conductor traces 205.

Flexible circuit 207 can be a polymer substrate upon which a series of electronic devices, for example, electrodes 208, can be mounted. In some embodiments, flexible circuit 207 can be polyimide, PEEK, polyacrylic, epoxy, fluoropolymers or a transparent conductive polyester film. Flexible circuit 207 can be mounted on top of skeleton member 201 (not shown in FIG. 2C).

In order to generate a strong and focused electrical field for stimulation and recording or neural activity, flexible circuit 207 can have a periodic array of electrodes 208. For example, a total of 350 electrodes 208 are shown in FIG. 2C, with 10 electrodes 208 along the traverse side of the array 200 and 35 electrodes 208 on the longitudinal side of the array 200. Possible electrode configurations include, but not limited to, hexagonal lattices and square lattices, as well as nonperiodic and quasiperiodic arrangements. While a periodic array of electrodes 208 is shown, the array need not be periodic and can have any number or configuration of electrodes necessary for the treatment required. In addition, the electrodes need not be uniform in size or shape across the array, and between-electrode spacing can also vary across the array. Possible electrode shapes include, but not limited to, circular, square, polygonal, or polygonal with rounded edges. Electrode diameters typically range from about 5 micrometers to about 500 micrometers in diameter, though both larger and smaller electrode sizes are possible.

In some embodiments, flexible circuit 207 can be a continuous sheet. In some embodiments, flexible circuit 207 can be slit by laser excision to form center and side panels to allow easier folding of conformable electrode array 200. In the slit configuration, the electrical components can be positioned such that no electrical components span across the fold line.

In some embodiments, electrodes 208 can be composed of a biocompatible and electrically conducting material. Electrodes can be made of materials including, but not limited to, platinum, iridium, gold, or nitinol. These metals may be electroplated over other materials, such as copper. Electrodes 208 also can be further coated with platinum-iridium or gold to improve conduction properties, biocompatibility, and radiopacity.

In some embodiments, the array of electrodes 208 supported on flexible circuit 207 can be used for recording of electrical signals generated by the brain in the regions surrounding the cerebral ventricles, or for electrically stimulating regions of the brain surrounding the cerebral ventricles. In some embodiments, electrodes 208 in the array can be designed and arranged for recording, stimulation, or both. Material and geometric considerations, as well as electrical impedance considerations, apply to optimizing for one mode of operation or the other. Arrays can be configured with recording electrodes alone, stimulation electrodes alone, a combination of types, or electrodes capable of operating in both modes. Electrode surfaces can be treated, for example through chemical etching or other roughening techniques, or through polymer coating, to optimize their effective surface area and modify their impedance for recording or stimulation.

In some embodiments, each electrode 208 can have an associated conductor trace 205. In some embodiments, conductor traces 205 can be used to connect electrodes 208 to recording, stimulation, and other computational apparatus outside the ventricular system. Conductor traces 205 can be aligned inside the loops of skeleton member 201, which can be threaded inside the loop and merge into a single signal cable 206. Cable 206 can exit the ventricular system and the skull along the insertion path of the device, which may be generated by an endoscope, as discussed below. In some embodiments, conductor traces 205 can be composed of any suitable biocompatible conductor, for example, gold. In some embodiments, conductor traces 205 can be gold at nine micrometers thick sandwiched inside flexible circuit 207. Cable 206 can pass through a narrow-diameter tract through the cerebral cortex and cortical white matter, to exit through a small burr hole surgically drilled through the skull at the time of initial implantation. Accordingly, and as discussed in detail below, electrode array 200 can be connected to an implantable power source, implanted microcomputer, and implanted mechanism for data telemetry and communication with external devices. In some embodiments, the power source and microcomputer can be external to the body.

In some embodiments, a biocompatible coating can be conformally coated on to the entire assembly as a moisture barrier and lubricating coating. In some embodiments, the entire assembly can be conformal coated with Parylene C, though other coatings may be used.

FIG. 2D shows an axial cross section of the conformal electrode array in an unfolded configuration according to an embodiment of the present disclosure. Corresponding to the perspective view in FIG. 2C, FIG. 2D includes skeleton member 201, side panel 202, center panel 203, stiffener 204, flexible circuit 207, and electrodes 208. This view also depicts that each panel 203, 202 is located in individual loops of skeleton member 201. Bold line 209 of the skeleton member 201 indicates its helical nature along the longitudinal axis of the device 200. The distribution of ten electrodes 208 on the traverse side of the electrode array is also shown in this cross section view, with four electrodes mounted on the flexible circuit 207 on central panel 203, and three electrodes mounted on the flexible circuit 207 on each side panel 202. Each line of the ten electrodes 208 is periodically aligned along the longitudinal side of the device 200. Many other array configurations are envisioned, as described above, as the total number of electrodes, their sizes, and the inter-electrode spacing can be varied. In particular, by reducing electrode size and electrode spacing, conformal arrays can be manufactured with large numbers of electrodes. For example, 10 micrometer diameter electrodes spaced at an inter-electrode spacing of 10 micrometers in a square lattice results in an array of 250,000 electrodes per square centimeter, or 1 million electrodes per four square centimeters of array surface area. In some embodiments, the electrodes can be about 20 micrometers in diameter and spaced at 20 micrometers. Generally, the inter-electrode spacing can be about one half the diameter of a neuron.

Figures 3A, 3B:
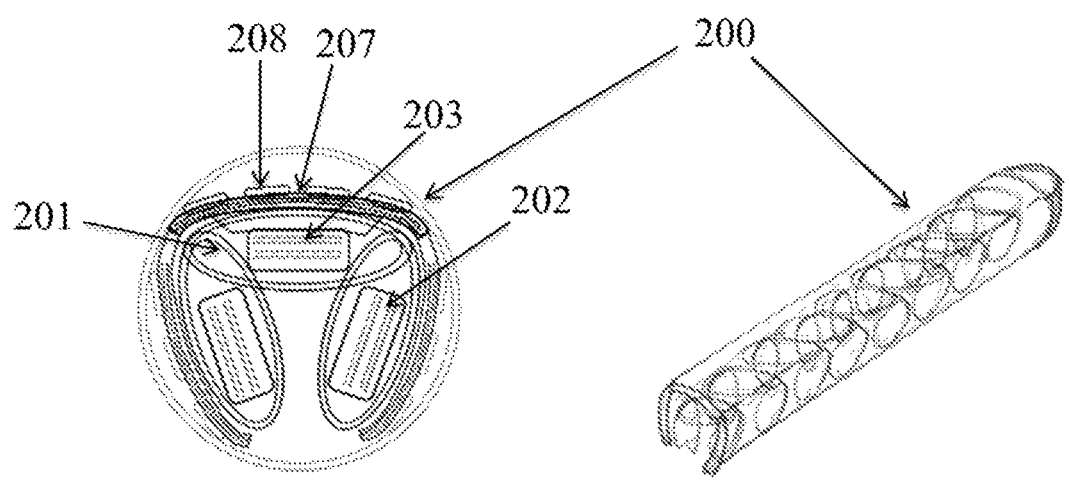
FIGS. 3A-3B depict the folded views of a conformal intraventricular electrode array, in accordance with embodiments of the present disclosure.

FIG. 3A (cross-section view) and FIG. 3B (perspective view) depict a folded configuration of conformal electrode array 200 according to an embodiment of the present disclosure. This folded configuration allows electrode array 200 to accommodate cannulation prior to deployment. FIG. 3A includes skeleton member 201, center panel 203, side panel 202, flexible circuits 207, and electrode contacts 208. The flexible mechanical structure can collapse into a narrow, axial configuration. In the embodiment depicted in FIG. 3A, with three loops in skeleton member 201, the three loops with two side panels 202 and center panel 203 collapse into a triangular shape. The associated flexible circuit 207 and electrodes 208 are also distributed on the sides of the triangular structure accordingly.

The collapsed configuration of the electrode array 200, as shown in the perspective view in FIG. 3B, is suitable for minimally invasive surgical deployment through a narrow cylindrical channel, with precision guidance from neuroimaging and under direct endoscopic visualization. In some embodiments, the narrow cylindrical channel can be less than two millimeters in width, such as the working channel of a standard neurosurgical endoscope. The present disclosure further includes a mechanism for converting electrode array 200 between the axial and deployed configurations. The conformal electrode array assumes a folded axial configuration inside the cylindrical channel to be transported into the implantation site inside the ventricle. The forward transition from axial to deployed is required during initial implantation. The reverse transition from deployed to axial is required for removal of the electrode array. During the reverse transition, a retraction force is applied through cable 206, the opening of the cylindrical channel compresses electrode array 200, the compression causes folding of array 200 into an axial configuration, which allows it to be removed from the implantation site back into the cylindrical channel.

In some embodiments, skeleton member 201 can be calibrated in a patient-specific manner to exert adequate pressure on the walls of the ventricular compartment to remain in fixed position and in contact with the inner ventricular surface, but without disrupting neurologic function and without significantly deforming the anatomic structures forming the boundaries of the ventricular compartment. In some embodiments, the contact pressure may be almost negligible, for example, just adequate to maintain the skeleton member 201 in the shape of the cavity, without exerting a physiologically significant pressure on the surrounding brain. The very minimal residual pressure can be accommodated over time by the brain with negligible clinical physiologic effect.

Prior neural electrical stimulation techniques have been one-dimensional or two-dimensional in nature. For example, some precedent stimulating electrode techniques that exploit array properties (as opposed to being simply geometrically arranged in an array, but operating as entirely independent electrodes) are described in the context of interleaved stimulation and current steering techniques for cochlear implants (Rubenstein (2004) *Curr. Opin. Otolaryngol. Head Neck Surg.* 5:444-448); (Choi et al. (2012) Cochlear Implant Research Updates, Chapter 5). The electrode arrays and neural substrates of interest in cochlear implant applications, however, are essentially one-dimensional. Recent developments in the context of deep brain stimulation (Timmermann et al. (2015) *Lancet Neurol.* 14:693-701) have demonstrated the value of current-steering techniques in deep brain stimulation, but those systems are also limited by being essentially one-dimensional as well. This revised approach to deep brain stimulation, using multiple current-sources, has recently been described and implemented (Timmermann et al. (2015) *Lancet Neurol.* 14:693-701), but the approach, while effective, remains limited in the sense that the electrode array is effectively linear, and requires intraparenchymal placement. The volume of brain tissue accessible for neural stimulation using deep brain simulation electrodes is extremely limited as compared with the planar intraventricular electrode arrays described here, which can assume three-dimensional shapes. Additionally, the deep brain stimulation electrodes must penetrate deep into the brain, damaging neural tissue along the insertion tract. The device disclosed herein relates to three-dimensional conformal electrode arrays, used to record from or stimulate three-dimensional volumes of neural tissue, which has not been accomplished by the prior art techniques.

An electrode array on a three-dimensional surface enables more versatile shaping of electric fields and more precise spatial targeting than conventional one-dimensional and two-dimensional electrode arrays. The ability to position arrays of many electrodes deep within the brain confers such arrays the further ability to generate tailored electrical fields, designed to stimulate an individual brain region with high spatial and temporal precision. In contrast to depth electrodes (such as those used in deep brain stimulation), for which intraparenchymal position is the primary determinant of the region stimulated, the regions accessible to stimulation by conformal arrays can be programmed with many degrees of freedom after deployment. Accordingly, stimulation by the described conformal electrode array does not require the direct proximity to the region of interest as does stimulation by linear depth electrodes such as those used in deep brain stimulation.

Due the high volumetric density of neurons within the brain, precise electrical stimulation of brain tissues requires a spatially and temporally focused electrical field. In some embodiments, a beam-formed electrical field can be created by the stimulation device. This can require a three-dimensional distribution of electrode contacts inside the brain. The conformable array described in the present disclosure provides three-dimensional distribution of electrodes, and enables beam-forming of the electrical field. Beam formation enables a focused stimulation of brain tissue, which is an advantage over existing technologies using one-dimensional electrodes. Further, the relatively large number of electrodes and the conformal design of the device enable a stimulation of three-dimensional volumes of neural tissue in precise manner.

FIGS. 4A-4D depict the formation of electrical fields using a single electrode tip, a one-dimensional linear electrode array, a two-dimensional electrode array, and a three-dimensional electrode array, according to one embodiment of the present disclosure. FIGS. 4A-4D depict a single tip electrode array 401, an omnidirectional (approximately isotropic) electric field with a spherical wavefront 402, a one-dimensional linear electrode array 403, a net electric field with a conical wavefront 404, a two-dimensional electrode array 405, a group of neurons and an associated bundle of axons 406, a three-dimensional electrode array 200 according to the present disclosure, and a single axon 407 stimulated by the three-dimensional electrode array.

Figures 4A, 4B, 4C, 4D:
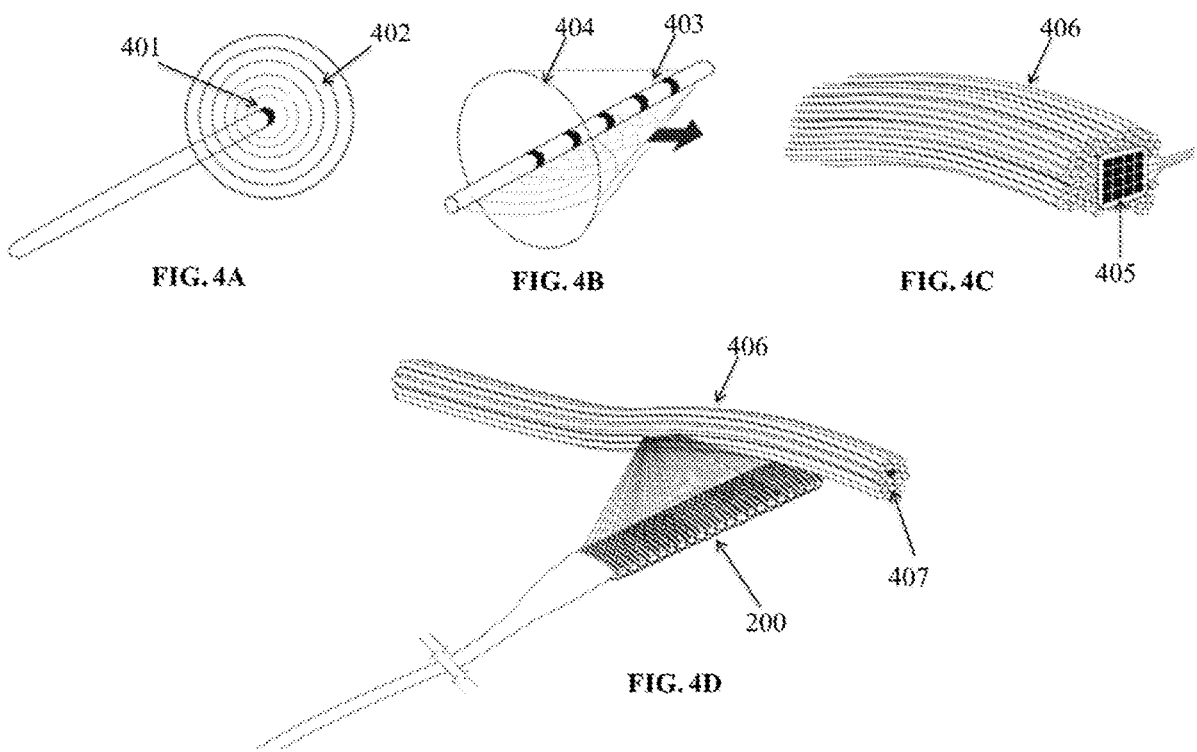
FIGS. 4A-4D depict the formation of electrical fields using a single electrode tip, one-dimensional linear electrode array, a two-dimensional electrode array, and a three-dimensional electrode array according to some embodiments of the present disclosure.

FIG. 4A shows a probe with a single electrode tip 401 that emits an omnidirectional electric field with a spherical wavefront 402. However, a single electrode cannot pinpoint direction when sensing a voltage. FIG. 4B shows a probe with a linear array of electrodes 403 that can either act as a series of individual point sources, or beam-form to direct a net electric field along an axis with a conical wavefront 404. Likewise, the linear array is only able to localize an incoming signal as originating from somewhere within a cone. FIG. 4C illustrates a two-dimensional array 405 directly in contact with a planar tissue surface containing neurons or electrically active cells, such as the retina or cerebral cortex. The axons 406 of these cells are also diagrammed. The array can stimulate small groups with which individuals electrodes are in contact. FIG. 4D illustrates a three-dimensional array 200 with a high density of electrode contacts according to the present disclosure. The flat array conforms to fit in a complex three-dimensional shape. The high-density electrode array beamforms in three dimensions to form a high-density electric field within a region small enough to stimulate specific neurons or groups of neighboring neurons. Likewise, when used as a sensor, the array is able to localize voltage sources precisely in three-dimensional space.

Several minimally invasive approaches can be used in contemporary neurosurgery for precise placement of devices within the cerebral ventricular system. (Mark M. Souweidance. Intraventricular Neuroendoscopy: A Practical Atlas. B. Braun, Aesculap Neurosurgery, Berlin) The conformal electrode array described herein is designed to integrate with several such techniques.

Figure 5:
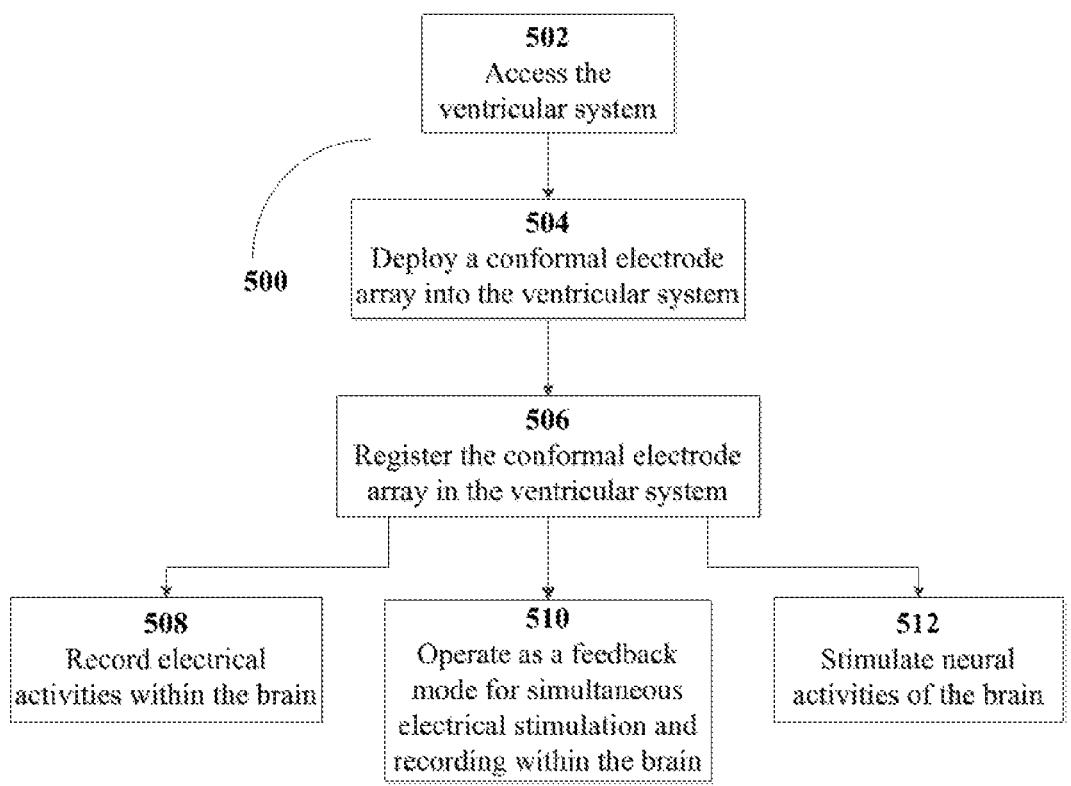
FIG. 5 depicts a flow chart of recording/stimulating electrical activities of the brain tissue using the conformal electrode arrays in the present disclosure.

FIG. 5 is a flow chart describing a method 500 for recording/stimulating the electrical activities within the brain, in accordance with an embodiment of the present disclosure. The first step in implantation of the electrode array is to cannulate the ventricular system 502 along a trajectory suitable for deployment of the array. The cannulation may be accomplished with a catheter alone, or with a ventricular neuroendoscope. Once the ventricular system has been cannulated, the array may be deployed 504 using fluoroscopic guidance, using its radio-opaque markers to guide positioning adjustments and final deployment position in real time. Alternatively, the array may be deployed under direct neuroendoscopic visualization.

Following deployment, the conformal electrode array changes from a collapsed state (as shown in FIGS. 3A-3B) to an unfolded configuration (as shown in FIGS. 2A-2D). The electrode array maintains contact with the ventricular surface, by exerting gentle pressure against the opposite wall of the ventricle. Portions of the electrode array may be made from a shape memory alloy, such as nitinol, and its preferred configuration assists in unfolding the array once it is deployed from (and no longer radially confined by) the channel of the cannulation.

Following array implantation is registration of the array 506. During this step, three-dimensional neuroimaging can be used to establish the final, deployed, spatial and anatomic orientation of an array, within the ventricular system. In some embodiments, elements of the conformal electrode arrays are radio-opaque, enabling unambiguous localization of each electrode in three-dimensional space and with respect to neighboring neuroanatomic structures using conventional neuroimaging modalities, such as computed tomography (CT). Registration can allow for precise stimulation and recording of neural tissue.

After deployment, as particular electrodes transmit electrical signals reflecting neuronal activity within the brain, it may be important in many applications to correlate the precise positions of implanted electrodes with their positions in three-dimensional space and with respect to anatomic structures. Such correlations can be established using CT imaging of the brain, provided the position of each electrode can be identified on CT. For this reason, to ensure detectability via CT and fluoroscopic imaging, certain components of the electrodes and the device are radio-opaque. For example, in some embodiments, radio opaqueness can be achieved using platinum titanium alloys. Analysis of such imaging data (typically high-resolution computed tomography, CT) forms the basis of the following:

(1) Computational determination of the anatomic origin of recorded electrical activity (in recording mode), and
(2) Computational structuring of the electrical fields generated by the array. After implantation, once the geometry of the deployed array is established, the net electrical field, and the resulting net current density function, is defined by the set of current and voltage settings assigned to the electrodes in the array.

Following registration, conformal electrode array can operate in a plurality of modes. For example, the device can operate in a recording mode 508, a stimulation mode 512 and a feedback mode 510.

In some embodiments, the device can include a recording mode. In the recording mode, a method of correlating imaging determining the position of the array relative to anatomic structures, with electrophysiologic recording data from which particular neural signals arise, to determine the spatial and neuroanatomic origin of those signals can be performed.

In some embodiments, the method can include a stimulation mode. In the stimulation mode, a method of correlating imaging determining the position of the array relative to anatomic structures, with computationally determined electric field geometry, so as to achieve precise image-guided electrical stimulation of neural structures can be performed. In some embodiments, this method can include a method of shaping the electric fields generated by the electrodes, so as to stimulate precise anatomic regions surrounding the cerebral ventricle; this configuration may be programmed prior to or following array implantation (based on patient-specific imaging, electrode recordings, behavior, response to therapy, or other data). A set of computational models, taking into account patient-specific anatomy based on neuroimaging obtained with the array in place, can be used to compute the anatomic origin of particular electrical signals recorded by the array. Similarly, a related set of such models can be used to shape the electrical fields and steer the electrical currents collectively generated by the array within surrounding neural tissue, in order to stimulate with anatomic and functional precision.

In some embodiments, in a feedback mode, electrical stimulation and recording can be performed simultaneously (by designating certain electrodes for stimulation and others for recording) or in an interleaved manner, in order to confirm efficacy of electrical stimulation in real-time, and in order to adapt electrical stimulation programs to real-time electrophysiologic responses. In some embodiments, the device can switch between modes after implantation. Each individual electrode in the array can be independently controlled. Once the electrode is implanted its geometric configuration and impedance are fixed. But any electrode can theoretically be used at any time for recording or simulation. In practice, arrays can be fabricated with specific electrodes designed either for recording or for stimulation, and the mode will rarely be changed after implantation. However, the current or voltage setting at each stimulation electrode can be independently controlled, as can stimulation timing, frequency, amplitude, and pulse-width of stimulations, and stimulation pulse shape, among other parameters.

The described conformal electrode array positioned in the cerebral ventricles can be minimally disruptive to normal brain tissue but can have extensive access to deep brain nuclei and fiber tracts that are otherwise difficult to access. Accordingly, the conformal array of ventricular neural electrodes disclosed herein has several major advantages over existing technologies.

(1) The electrodes do not damage normal brain tissue. In analogy to cortical surface (ECoG) electrodes, the described conformal electrode array lines the inner surface of the ventricular system, without penetrating brain tissue. By contrast, conventional approaches to recording and simulation deep within the brain has required placement of depth electrodes that damage normal brain tissue along the insertion trajectory.
(2) The electrodes in the described conformal array gain extensive, high-resolution access to large regions deep within the brain that are difficult to access except with a small number of depth electrodes, each of which is limited to recording from or stimulating a small volume.

Figures 6A, 6B, 6C:
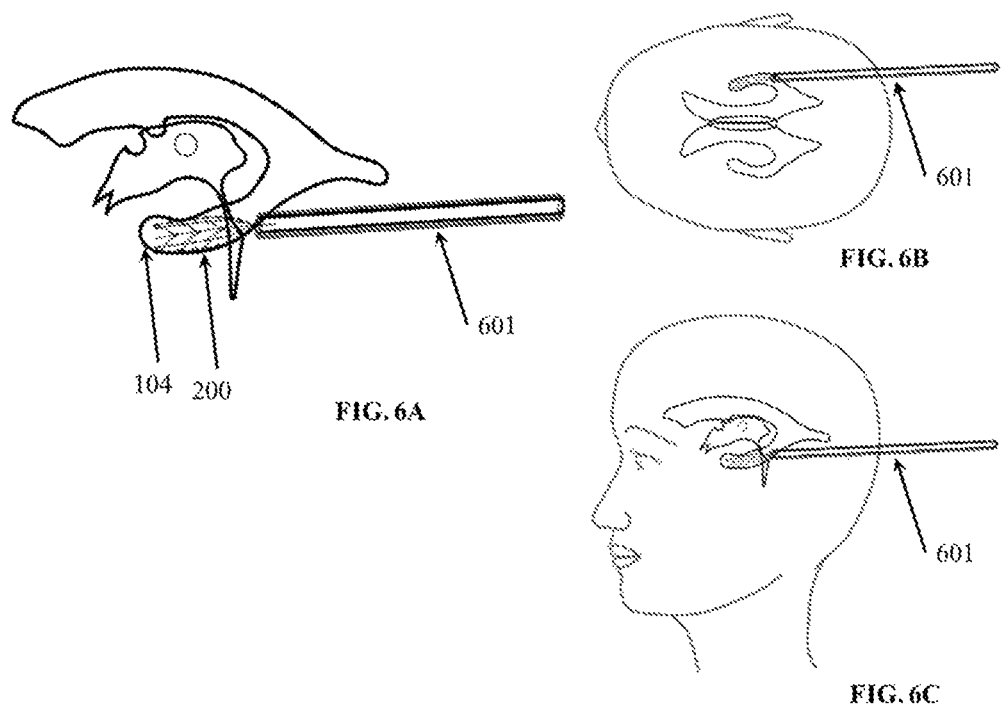
FIGS. 6A-6C depict endoscopic insertion of a conformal electrode array into the temporal horn of the right lateral ventricle in a human patient, in accordance with embodiments of the present disclosure.

FIGS. 6A-6C depict a deployed conformal intraventricular electrode array using a cannula, in accordance with embodiments of the present disclosure. FIGS. 6A-6C depicts cannula 601, conformal electrode array 200, and temporal horn 104 of the human brain. In particular, FIGS. 6A-6C illustrates endoscopic insertion of a conformal electrode array into the temporal horn of the right lateral ventricle of the brain in a human patient. An endoscope is used to gain access to the temporal horn in minimally invasive fashion. Specifically, FIG. 6C depicts a cross-section of a patient with deployed conformal intraventricular electrode array in a sagittal view (from the left), FIG. 6A depicts an exploded view of FIG. 6C, FIG. 6B depicts an axial view (from the top). Array 200 assumes a narrow axial configuration when confined to the inner channel of the cannula 601, then expands when unsheathed from the cannula 601 in the temporal horn 104 of the lateral ventricle.

Figure 7:
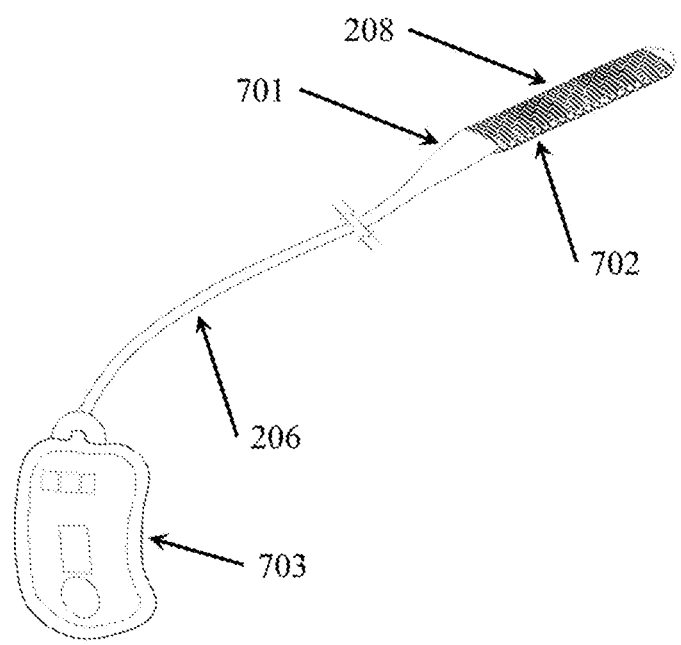
FIG. 7 depicts a mechanical packaging of one conformal electrode array, in accordance with embodiments of the present disclosure.

FIG. 7 illustrates packaging of the conformal electrode array designed for insertion in the temporal horn of the lateral ventricle, and for electrical recording from the hippocampus from within the temporal horn. FIG. 7 includes electrode contacts 208, flexible substrate 701, scaffolding 702, bundled lead wires 206 as a connector, and hermetically sealed package 703. The scaffolding can be composed of skeleton member 201, side panels 202, center panel 203, and stiffener 204 (as shown in FIGS. 2A-2D. The flexible substrate can be composed of flexible circuit 207 mounted on the scaffolding. Substrate 701 is supported by scaffolding 702 that ensures the electrode array maintains contact with the ventricular surface, by exerting gentle pressure on the opposite wall of the ventricle. Bundled lead wires 206 exit the ventricular system and the skull along the insertion path of the endoscope, and enters hermetically sealed package 703. Package 703 may be constructed entirely from silicone, and implanted between skull and scalp. The configuration and implantation technique for this package are similar to those of an Ommaya reservoir, known in the neurosurgical art and commonly used for the delivery of chemotherapy in neuro-oncology. This package contains implantable electronic elements for neural signal recording and wireless transmission.

As the leads from the recording electrodes exit the brain, they form a bundle that is tunneled through a small-diameter hole surgically drilled in the skull. After exiting the skull, this bundle may be tunneled in a subcutaneous layer to a microcomputer or other device designed to power the electrodes, store recording data, store stimulation parameters, and coordinate wireless data telemetry with external devices. These active electronic components are contained within the hermetic package. In such a configuration, the conformal electrode array permits long-term electroencephalographic monitoring of patients in the ambulatory setting, as there is no fluidic communication between the brain and the outside world, and hence no major risk of intracranial infection. In this configuration, the monitoring capabilities of the conformal, minimally invasive system disclosed here offer an option not available using conventional grid and strip electrodes, which are implanted via craniotomy, tunneled through dura, skull, and skin, and permit leakage of cerebrospinal fluid and a conduit between the brain and the outside world. Epilepsy patients undergoing monitoring using such techniques, which represent the present state of the art, must be monitored in a hospital setting until the recording electrodes are removed. Furthermore, in the current state of the art, removal of the electrodes requires a second operation for electrode removal, repair of the dura membrane, and reaffixing of the removed portion of the skull.

On the other hand, the system disclosed herein does not preclude monitoring using such conventional techniques. Using the system disclosed herein, device leads may also, temporarily, be tunneled through the skin for patient monitoring in a conventional epilepsy monitoring unit.

FIG. 8A illustrates another application of the conformal electrode according to an embodiment of the present disclosure. FIGS. 8A-8B depicts conformal electrode array 200, left temporal horn 104, left hippocampus 801, connector 206, and hermetically sealed package 703. Conformal electrode array 200 can be implanted in the temporal horn 104 of the left lateral ventricle, for electrical recording from the left hippocampus 801 from within the temporal horn 104. The electrode leads from the entire array are bundled in connector 206, which exits the ventricular system and the skull along the insertion path of the previously used endoscope. Connector 206 enters hermetically sealed package 703. Package 703 may be implanted between skull and scalp, and contains implantable electronic elements for neural signal recording and wireless transmission. FIG. 8B illustrates the implanted system of FIG. 8A in sagittal cross-section, seen from the left, indicating the positions of conformal array 200 and hermetically sealed package 703.

Figure 9:
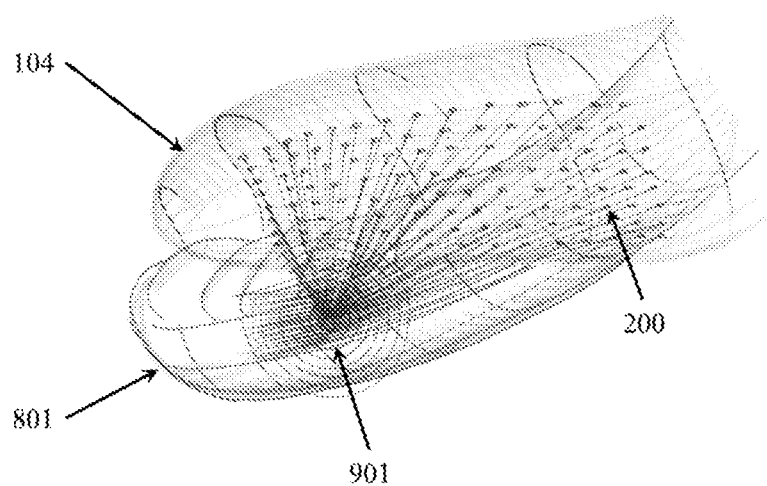
FIG. 9 depicts detection of epileptogenic electrical activity within the hippocampus by a conformal array of electrodes, in accordance with embodiments of the present disclosure.

FIG. 9 shows detection of epileptogenic electrical activity using the conformal electrode array, in accordance with an embodiment of the present disclosure. FIG. 9 includes conformal electrode array 200, temporal horn 104, hippocampus 801, and an epileptogenic focus 901. As shown in FIGS. 7 and 8A-8B, conformal array 200 is positioned adjacent hippocampus 801 of temporal horn 104. In this position, conformal array 200 stimulates and detects epileptogenic electrical activity within the hippocampus in the temporal horn of the lateral ventricle. The three-dimensional distribution of electrodes enables a very precise and sensitive detection of electrical activity from a small epileptogenic focus.

Neurologic disorders such as Parkinson's disease and epilepsy can be treated using spatially targeted electrical recording and stimulation of specific neuroanatomic structures. Electrical stimulation of deep brain targets is an important modality in the treatment of Parkinson's disease, essential tremor, and certain (thalamic) pain syndromes. The efficacy of neuro stimulation-based therapy is highly dependent on the ability to stimulate the correct target with precision. In certain cases, it is difficult or impossible to introduce a conventional intraparenchymal depth electrode into the target without simultaneously generating a lesion associated with electrode placement.

A grid of intraventricular electrodes enables highly versatile shaping of electrical fields, with the ability to design and modify the electric field within and surrounding targets in the traditional targets used during deep brain stimulation, including the thalamus, subthalamic nucleus, globus pallidus, and substantia nigra.

A revised approach to deep brain stimulation, using multiple current-sources, has recently been described and implemented (Timmermann et al. (2015) *Lancet Neurol.* 14:693-701), but this approach, while effective, remains limited in the sense that the electrode array is effectively linear, and requires intraparenchymal placement. The volume of brain tissue accessible for neural stimulation is considerably more limited than in the case of the intraventricular electrode array described here.

Figures 10A, 10B, 10C:
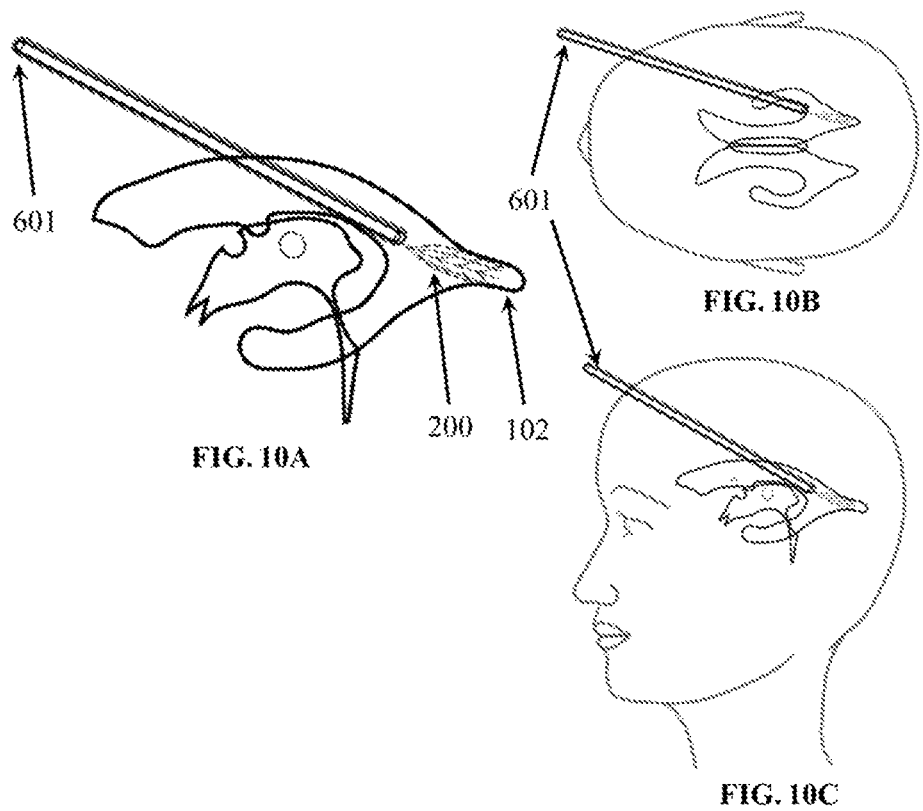
FIGS. 10A-10C depict endoscopic insertion of a conformal electrode array into the occipital horn of the right lateral ventricle in a human patient, in accordance with embodiments of the present disclosure.

FIGS. 10A-10C illustrates endoscopic insertion of a conformal electrode array 200 into the occipital horn 102 of the right lateral ventricle in a human patient. An endoscope 601 is used to gain access to the temporal horn in minimally invasive fashion. The trajectory of the endoscope is shown in sagittal views FIGS. 10A and 10C (from the left), and in an axial view FIG. 10B (from above). The array assumes a narrow axial configuration when confined to the inner channel of the endoscope, then expands when unsheathed from the endoscope in the occipital horn of the lateral ventricle. From that position it can stimulate the optic radiations as they converge toward the visual cortex in the occipital lobe.

Figure 11:
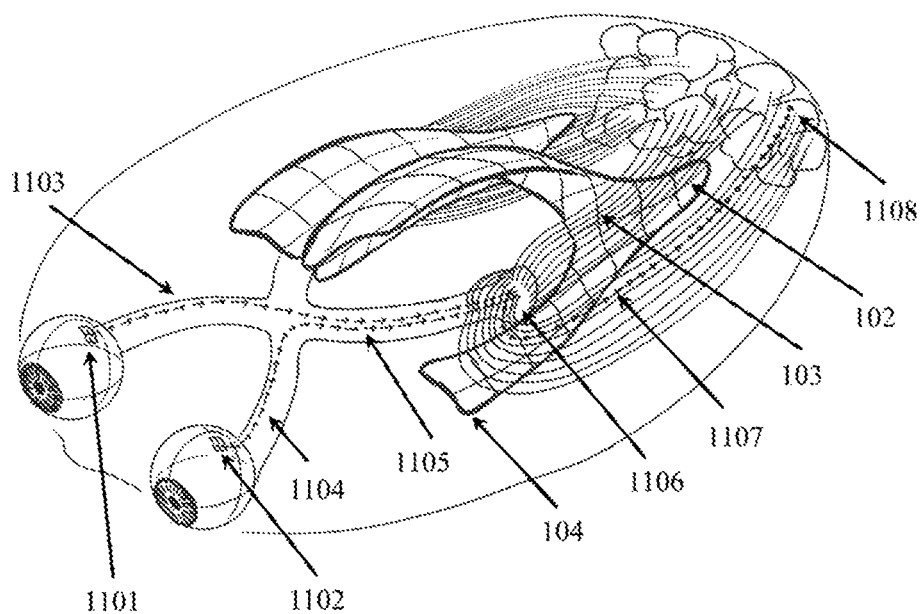
FIG. 11 depicts the pathways of the human visual system in relation to the cerebral ventricles.

FIG. 11 illustrates the pathways of the human visual system in relation to the cerebral ventricles, including right eye 1101, left eye 1102, right optic nerve 1103, left optic nerve 1104, left optic tract 1105, left lateral geniculate nucleus 1106, left temporal optic radiations 1107, visual cortex 1108, occipital horn 102, temporal horn 104, and atrium 103, as illustrated above.

An object in the visual field forms simultaneous images on the retinas of the right eye 1101 and the left eye 1102. The long axons of ganglion cells in the right and left retinas form the right optic nerve 1103 and the left optic nerve 1104, respectively. As illustrated here, an object in the right superior quadrant of the visual field forms a retinal image in the left inferior quadrant of the retina, and the axons of the retinal ganglion cells from both eyes that sense the formed images follow the left optic tract 1105 to the left lateral geniculate nucleus 1106. Visual information from the right inferior visual field exits the lateral geniculate nucleus via the left parietal optic radiations 1007, and visual information from the right superior visual field exits the left lateral geniculate nucleus via the left temporal optic radiations 1007 (arrows). The left temporal and parietal optic radiations converge on the visual cortex 1108 of the left occipital lobe. The temporal lobe optic radiations follow the surface of the temporal horn 104 of the lateral ventricle. The parietal lobe optic radiations follow the surface of the lateral ventricle near the atrium 103 of the ventricle. The occipital horn 102 of the lateral ventricle projects into the occipital lobe toward the visual cortex 1108.

Figures 12A, 12B:
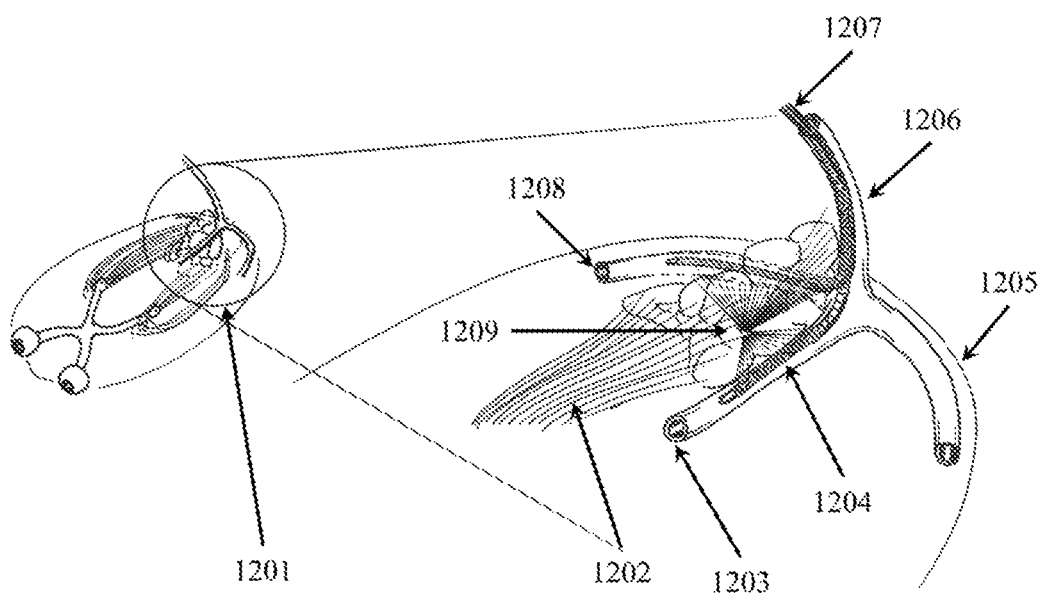
FIGS. 12A-12B depict electrode arrays implanted within the superior sagittal sinus, transverse sinus, and straight sinus, in relation to the structures within the human visual system that they are designed to stimulate.

FIG. 12B illustrates an exploded view of the cerebral venous sinuses 1201 shown in FIG. 12A within the human visual system, including optic radiations 1202, straight sinus 1203, left transverse sinus 1205, superior sagittal sinus 1206, and right transverse sinus 1208, stimulating points for implanted electrode arrays 1209 and the electrodes 1204 and 1207 implanted inside the sinus system. The inset FIG. 12A illustrates the relationship of the major cerebral venous sinuses 1201 to the entire visual system, as illustrated in FIG. 11. These major cerebral venous sinuses meet in the occipital region, and are positioned adjacent to visual cortex. Optic radiations 1202 converge in the visual cortex. The right transverse sinus 1208 follows the surface of the right visual cortex in the right occipital lobe, and left transverse sinus 1205 follows the surface of the left visual cortex in the left occipital lobe. The superior sagittal and straight sinuses are positioned between the right and left visual cortexes. Electrodes 1207 within the superior sagittal sinus 1206, straight sinus 1204, and right transverse sinus 1208 are illustrated. Such electrodes are capable of recording from and stimulating points 1209 such as in adjacent visual cortex, to generate visual percepts in predictable and reproducible fashion.

Minimally invasive stimulation of the optic radiations may provide an approach to delivering visual stimuli to the blind. Several approaches to electrical stimulation of the visual pathways have been experimentally demonstrated and reviewed (Pezaris et al. (2009) *Neurosurg. Focus* 27:E6), as potential approaches to developing a visual prosthesis for the blind. All such approaches, to date, have used intraparenchymal depth electrodes, which would require introducing lesions into the very tracts that carry visual information, as the depth electrodes would need to penetrate the cortical regions or white matter tracts of interest.

Phosphenes, visual phenomena often described as transient "flashes of light" related to electrical stimulation, are common side effects of deep brain stimulation during initial intraoperative placement and testing of the electrodes, and subsequent programming. In the context of deep brain stimulation targeting the thalamus and subthalamic nucleus, for example, by high-amplitude stimulation, can give rise to fringe electrical fields that cause depolarization of axons in the optic tracts, giving rise to transient visual sensations. While these effects are unwanted in the context of deep brain stimulation, they confirm that it is possible to generate visual sensations in a reproducible manner by controlling the electric field generated by electrodes placed at a distance from the optic pathway, rather than directly into the pathway itself (at the level of the optic tracts, lateral geniculate nuclei, optic radiations, or visual cortex, for example).

The conformal array of intraventricular electrodes disclosed herein can enable highly versatile shaping of electrical fields, with the ability to target locations along the visual pathway, including the optic tracts, lateral geniculate nuclei, optic radiations, and visual cortex. An adaptive, computational approach to mapping the visual pathways using electrical stimulation and recording, with or without collaboration from the subject, holds promise for a prosthesis to restore vision to the visually impaired.

In some embodiments, endovascular, venous sinus stent electrode arrays may also be deployed within the major venous sinuses (superior sagittal sinus, transverse sinuses, and straight sinus) that immediately border the surfaces of the visual cortex. The visual cortex in the occipital lobe is a natural target for stimulation to generate visual percepts, as it contains a retinotopic map of visual space. Simulation of the visual cortex is facilitated by access to the major venous sinuses (superior sagittal sinus, transverse sinuses, and straight sinus) bordering the occipital cortex, using electrodes deployed on scaffoldings apposed to the walls of the venous sinuses, such as venous stents. Such stents are ultimately integrated into the blood vessel walls, covered by thin layers of endothelium.

Figure 13:
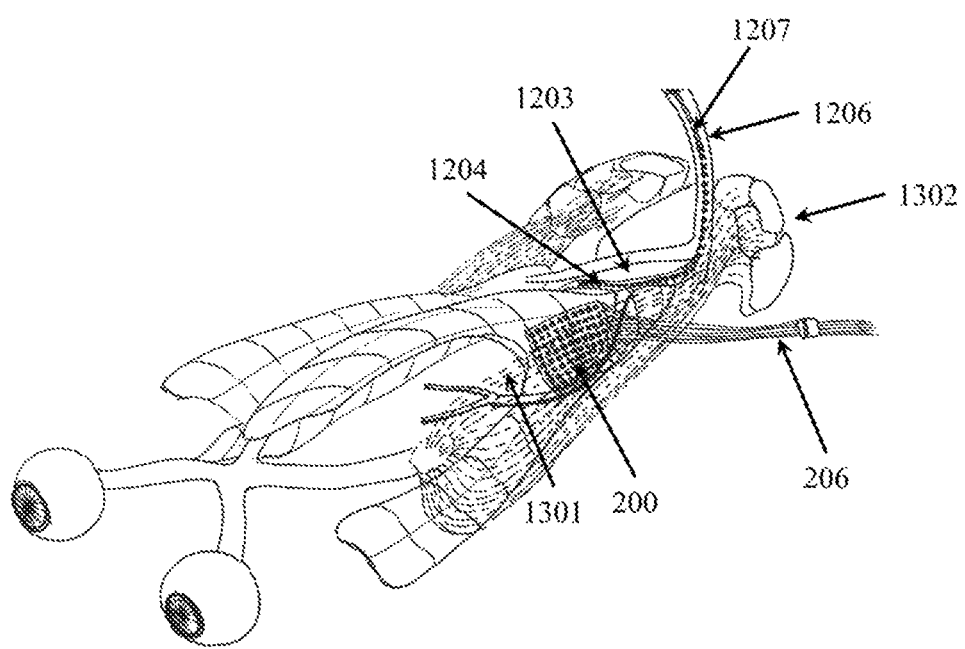
FIG. 13 depicts electrodes within the major cerebral venous sinuses and the ventricular system, in relation to the visual pathways of the human brain.

FIG. 13 illustrates electrodes within the major cerebral venous sinuses and the ventricular system, in relation to the visual pathways of the human brain, which includes conformal electrode array 200, its corresponding connector 206, straight sinus 1203 and implanted endovascular electrode array 1204, superior sagittal sinus 1206 and implanted endovascular electrode array 1207, parietal optic radiations 1301 and occipital lobes 1302. A conformal electrode array 200 is positioned in the atrium of the left lateral ventricle, adjacent to parietal optic radiations 1301. Connector 206 exits the ventricular system and the brain. An endovascular electrode array 1204 and 1207 is positioned in the superior sagittal sinus 1206 and the straight sinus 1203, adjacent to the visual cortexes in the right and left occipital lobes 1302. Each electrode array is constructed to conform to the walls of its respective compartment: the ventricular array conforms to the ventricular surface, while the venous array conforms to the walls of the venous sinus. In one embodiment of the present disclosure, the endovascular electrode can be microfabricated on a conformal, flexible circuit, with inter-electrode spacing corresponding to cellular size (typical neuron cell bodies are about 50 micrometers in diameter). In another embodiment, the flexible circuit can be a polymer substrate upon which a series of electronic devices, for example, electrodes, can be mounted. In some embodiments, flexible circuit can be polyimide, PEEK, polyacrylic, epoxy, fluoropolymers or a transparent conductive polyester film. In yet another embodiment, the endovascular electrode contains a high density of electrodes. In a specific embodiment, the endovascular electrode array has electrodes with about 10 to 20 micrometers in diameter, spaced at about 10 to 20 micrometers from each other, this configuration can include about 100,000 electrodes per square centimeter, about 200,000 electrodes per square centimeter, or about 250,000 electrodes per square centimeter. That is, the endovascular electrode array can have a similar electrode density as the ventricular conformal electrode array.

Targeted electrical stimulation of white matter tracts transected by hemorrhage or stroke has the potential to restore neurologic function. Several approaches to electrical stimulation of the motor pathways have been experimentally demonstrated and reviewed, as potential approaches to developing a neural prostheses for paralyzed individuals and amputees (Wolpaw et al. (2012) *Mayo Clin. Proc.* 87:268-279), and as approaches to restoring function in patients paralyzed or partially paralyzed due to stroke (Boyd et al. (2015) *Front Neurol.* 6:226). Some such major and promising approaches, to date, have used cortical surface electrodes or intraparenchymal depth electrodes, which can only be placed through brain surgery, and which can require introducing lesions into the very tracts that carry motor information, as the electrodes need to penetrate the cortical regions or white matter tracts of interest.

Figure 14:
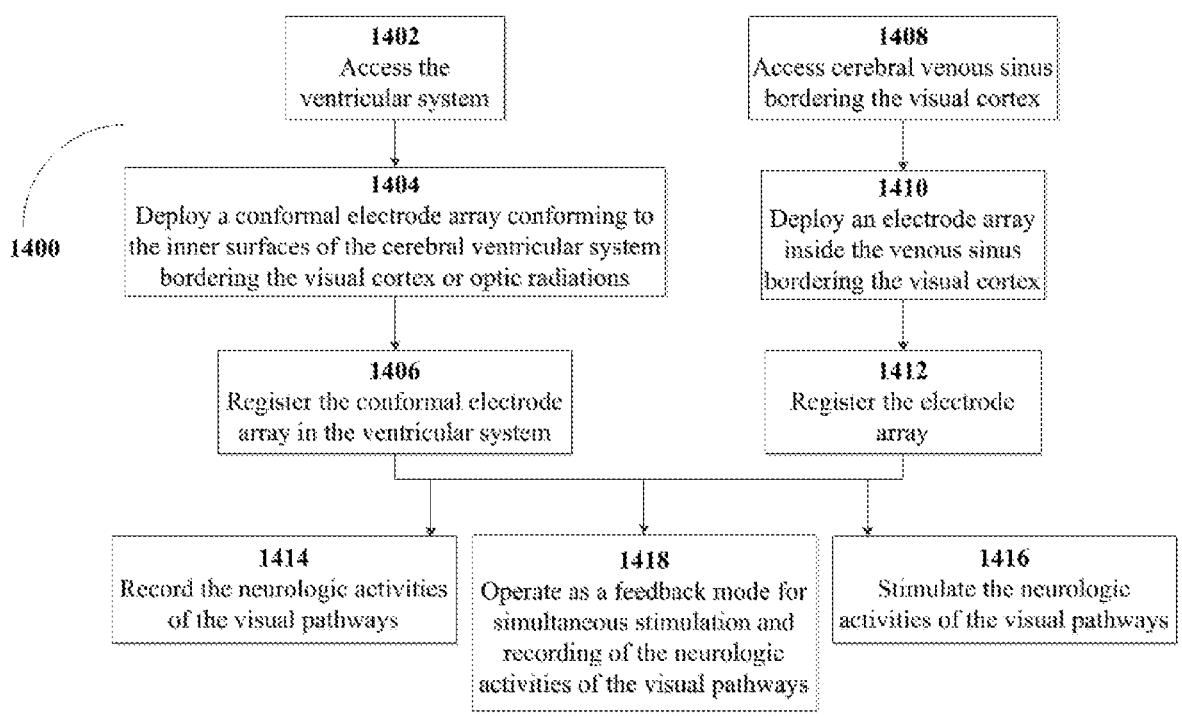
FIG. 14 depicts a flowchart of generating visual percepts using the conformal electrode arrays in the present disclosure.

FIG. 14 is a flow chart describing a method 1400 for generating visual percepts using the conformal electrode arrays, in accordance with an embodiment of the present disclosure. Simultaneous electrode array implantation in the occipital horn of the lateral ventricle and the major venous sinuses bordering the occipital cortex permits versatile, three-dimensional electric fields to be configured in the visual cortex, to generate potentially high-resolution visual percepts, potentially on the basis of still or video images recorded from the outside world, in the context of a visual prosthesis.

The first step is to access the ventricular system 1402 and deploy the conformal electrode array to the inner surfaces of the cerebral ventricular system bordering the visual cortex or optic radiations 1404. In one embodiment of the present disclosure, deployment of the conformal electrode array is through cannulation, this may be accomplished with a catheter alone, or with a ventricular neuroendoscope. Following deployment, the conformal electrode array changes from a collapsed state (as shown in FIGS. 3A-3B) to an unfolded configuration (as shown in FIGS. 2A-2D). The electrode array maintains contact with the ventricular surface, by exerting gentle pressure against the opposite wall of the ventricle. Following deployment, the conformal electrode array is registered in the ventricular system 1406. In this step, the position and orientation of the conformal electrode array can be identified via neuroimaging. Following registration, the electrode arrays can be used to record the electrical activities of the visual pathways 1414, to stimulate the neurologic activities of the visual pathways 1416, or operate as a feedback mode 1418 for simultaneous electrical stimulation and recording of the neurologic activities of the visual pathways.

Optionally, cerebral venous sinuses bordering the visual cortex are accessed 1408 to deploy an electrode array 1410. In one embodiment of the present disclosure, the deployment can be done by venous catheterization, for example, via a femoral vein or internal jugular vein, using established methods known to those skilled in the art. After registration of the electrode in the venous sinuses 1412, this electrode can be used together with the conformal electrode arrays inside the ventricle to operate as a recording mode 1414, a stimulation mode 1416, or a feedback mode 1418. In one embodiment of the present disclosure, the conformal electrode arrays placed in the ventricular system are described in FIGS. 2A-2D and FIGS. 3A-3B. In another embodiment of the present disclosure, an endovascular electrode is placed in a cerebral venous sinus bordering the visual cortex. In a some embodiments of the present disclosure, the intraventricular and endovascular electrodes synergistically work together, the endovascular electrodes generate additional electrical fields to precisely stimulate/record the neurologic activities from the visual pathways.

The present disclosure can be used for stimulation of optic radiations and other components of the visual pathway for a visual prosthesis. In some embodiments, the aggregate electric field and current density function of the implanted array is configured to stimulate a set of targets within the visual pathways of the brain, including targets within the optic tracts, lateral geniculate bodies, and optic radiations. In each of these targets, a topological representation of images projected on the retina is preserved in the organization of neuronal cell layers and corresponding axons, facilitating rational stimulation patterns intended to generate perception of meaningful images. The optic radiations of the temporal and parietal lobes are natural targets for stimulation to generate visual percepts, as well. Stimulation of these parts of the visual pathway are facilitated by access to the body, atrium, occipital horn, and temporal horn of the lateral ventricle, as the optic radiations pass adjacent to the walls of the ventricles and can be stimulated from within the ventricles.

The occipital visual cortex is also a natural target for stimulation to generate visual percepts, and stimulation of the visual cortex is facilitated by access to the major venous sinuses (superior sagittal sinus, transverse sinuses, and straight sinus) that immediately border the surfaces of the visual cortex.

In these embodiments as well, the conformal electrode array has advantages over traditional depth and microelectrode arrays, as the conformal array can be configured to simulate the fields and current densities generated by multiple arrays of electrodes implanted at many sites within the optic pathways, without damaging or displacing brain tissue in those pathways, and the configuration can be changed based on individual patient experience over time. Implanted electrodes or microelectrode arrays, by contrast, cannot easily be moved after implantation without risk of significant brain injury, and implantation would damage the optic pathways. Furthermore, the set of targets stimulated can be chosen in a three-dimensional manner that would be difficult or impossible to achieve using any existing depth electrodes or microelectrode array, and difficult-to-access parts of the visual pathways can be targeted noninvasively.

In such visual prosthetic applications, stimulation could be delivered in a programmed manner, based on data acquired by external sensors such as video cameras. In some embodiments, the external sensor can be a wearable camera. For example, the cameras can be worn on the eye of a user. Or, in other embodiments, the external sensor can be a video device suitable to be worn by a user in the form of glasses or goggles, wherein the glasses frame can support a camera, electronics and a battery. In some embodiments, the described visual prosthesis can provide a high pixel count of 10,000 pixels, 100,000 pixels, 250,000 pixels, or more to restore, replicate, or augment normal human vision.

While the disclosure has been described in connection with certain embodiments, it is to be understood that the disclosure is not to be limited to the disclosed embodiments but, on the contrary, is intended to cover various modifications and equivalent arrangements included within the spirit and scope of the disclosure, which scope is to be accorded the broadest interpretation so as to encompass all such modifications and equivalent structures as is permitted under the law.

The invention claimed is:

1. A method of electrically stimulating or recording from portions of a brain that relate to vision using an endovascular electrode array within a venous sinus proximate to a visual cortex, the method comprising:
   determining a portion of the visual cortex for electrical stimulation;
   accessing previously stored registration information regarding a location of the endovascular electrode array within the venous sinus;
   selecting one or more electrodes in the endovascular electrode array based on the registration information; and
   electrically stimulating or recording from the determined portion of visual cortex with the selected electrodes.

2. The method of claim 1, comprising forming an electrical field distributed in a three-dimensional space using the selected electrodes.

3. The method of claim 1, comprising localizing electrical activity in the brain using the selected electrode distributed in a three-dimensional space.

4. The method of claim 1, comprising registering the endovascular electrode array to obtain its orientation and position within the venous sinus.

5. The method of claim 4, wherein registering comprises neuroimaging.

6. The method of claim 1, comprising inserting the endovascular electrode array into the venous sinus via a minimally invasive insertion technique.

7. The method of claim 1, comprising inserting the endovascular electrode into the venous sinus via a cannula or catheter.

8. The method of claim 1, comprising receiving visual images from an external imaging system in electrical communication with the plurality of electrodes.

9. The method of claim 1, comprising receiving visual images from an external imaging device mounted on the eye of a user, a glass, or a goggle.

10. The method of claim 1, comprising providing an image having a high pixel count of at least 10,000 pixels to approximate, restore, or augment normal human vision.

11. The method of claim 1, comprising inserting the endovascular electrode array into the venous sinus so that the endovascular electrode array is disposed in a three-dimensional configuration.

\* \* \* \* \*